United States Patent
Ishihara

(10) Patent No.: US 9,207,179 B2
(45) Date of Patent: Dec. 8, 2015

(54) FLUORESCENCE OBSERVATION APPARATUS

(71) Applicant: OLYMPUS CORPORATION, Tokyo (JP)

(72) Inventor: Yasushige Ishihara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/738,010

(22) Filed: Jun. 12, 2015

(65) Prior Publication Data

US 2015/0276602 A1  Oct. 1, 2015

Related U.S. Application Data

(63) Continuation of application No. PCT/JP2013/082437, filed on Dec. 3, 2013.

(30) Foreign Application Priority Data

Dec. 13, 2012  (JP) ................................ 2012-272305

(51) Int. Cl.
*G01N 21/64* (2006.01)

(52) U.S. Cl.
CPC .... *G01N 21/6456* (2013.01); *G01N 2021/6471* (2013.01); *G01N 2201/061* (2013.01)

(58) Field of Classification Search
CPC .... A61B 1/043; A61B 5/0071; A61B 5/0084; G01N 21/6456
USPC ...................................................... 250/459.1
See application file for complete search history.

(56) References Cited

U.S. PATENT DOCUMENTS

| | | | |
|---|---|---|---|
| 2002/0035330 A1* | 3/2002 | Cline et al. | 600/476 |
| 2003/0001104 A1* | 1/2003 | Sendai et al. | 250/458.1 |
| 2011/0152614 A1* | 6/2011 | Takei | 600/109 |

FOREIGN PATENT DOCUMENTS

| | | |
|---|---|---|
| EP | 2526853 A1 | 11/2012 |
| JP | 2005-204958 A | 8/2005 |
| JP | 2007-125245 A | 5/2007 |
| JP | 2007-215927 A | 8/2007 |
| JP | 4533673 B2 | 9/2010 |
| WO | WO 2011/111619 A1 | 9/2011 |

OTHER PUBLICATIONS

International Search Report dated Mar. 4, 2014 issued in PCT/JP2013/082437.

* cited by examiner

*Primary Examiner* — Marcus Taningco
(74) *Attorney, Agent, or Firm* — Scully, Scott, Murphy & Presser, PC

(57) ABSTRACT

A fluorescence observation apparatus, including: a light source configured to irradiate a subject with reference light and excitation light; and one or more processors including hardware, wherein the one or more processors are configured to implement: a fluorescence-image generating portion configured to generate a fluorescence image; a reference-image generating portion configured to generate a color reference image; an extraction portion configured to extract a fluorescence region from the fluorescence image; a motion-effect generating portion configured to generate a frame image bringing about an effect that is visually time-varying with a variation quantity depending on a gradation value of the fluorescence region, in a region corresponding to the fluorescence region; and a synthesis portion configured to add the frame image to any of a plurality of color-component images constituting the reference image to synthesize a synthetic image.

10 Claims, 11 Drawing Sheets

FLUORESCENCE OBSERVATION APPARATUS

CROSS-REFERENCE TO RELATED APPLICATIONS

This is a continuation of International Application PCT/JP2013/082437, with an international filing date of Dec. 3, 2013, which is hereby incorporated by reference herein in its entirety. This application claims the benefit of Japanese Patent Application No. 2012-272305, filed on Dec. 13, 2012, the content of which is incorporated herein by reference.

TECHNICAL FIELD

The present invention relates to a fluorescence observation apparatus.

BACKGROUND ART

In the related art, there have been known fluorescence observation apparatuses that acquire a reference image, such as a white-light image, capturing the morphology of a subject, and a fluorescence image visualizing a lesion by capturing fluorescence from the subject, and that display the lesion within the fluorescence image with the lesion superimposed on the reference image (for example, see Patent Literatures 1 and 2).

In Patent Literature 1, the fluorescence image is added to any of a red-component image, a green-component image, and a blue-component image constituting the color reference image to thereby display the lesion as a red, green, or blue region on the reference image. In this case, since the reference image includes information on original gradation values, i.e. information on the morphology of the subject, in a region displaying the lesion, the morphology of the lesion can also be observed. In Patent Literature 2, the region of the lesion in the reference image is filled with a false color. In this case, the visibility of the lesion will be improved.

CITATION LIST

Patent Literature

{PTL 1} the Publication of Japanese Patent No. 4533673
{PTL 2} Japanese Unexamined Patent Application, Publication No. 2005-204958

SUMMARY OF INVENTION

The present invention provides a fluorescence observation apparatus including: a light source configured to irradiate a subject with reference light and excitation light; and one or more processors comprising hardware, wherein the one or more processers are configured to implement: a fluorescence-image generating portion configured to generate a fluorescence image based on fluorescence produced in the subject due to irradiation with the excitation light; a reference-image generating portion configured to generate a color reference image based on return light returning from the subject due to irradiation with the reference light; an extraction portion configured to extract, from the fluorescence image generated by the fluorescence-image generating portion, a fluorescence region having a gradation value equal to or higher than a prescribed threshold; a motion-effect generating portion configured to generate a frame image that is assigned a time-varying gradation value so as to bring about an effect that is visually time-varying with a variation quantity depending on a gradation value of the fluorescence region, in a region corresponding to the fluorescence region extracted by the extraction portion; and a synthesis portion configured to add the frame image generated by the motion-effect generating portion to at least one of a plurality of color-component images constituting the reference image, to synthesize a synthetic image from the plurality of color-component images including the color-component image that the frame image has been added to.

DESCRIPTION OF EMBODIMENT

A fluorescence observation apparatus 1 according to one embodiment of the present invention will be described below with reference to FIGS. 1 to 5.

Figure 1:
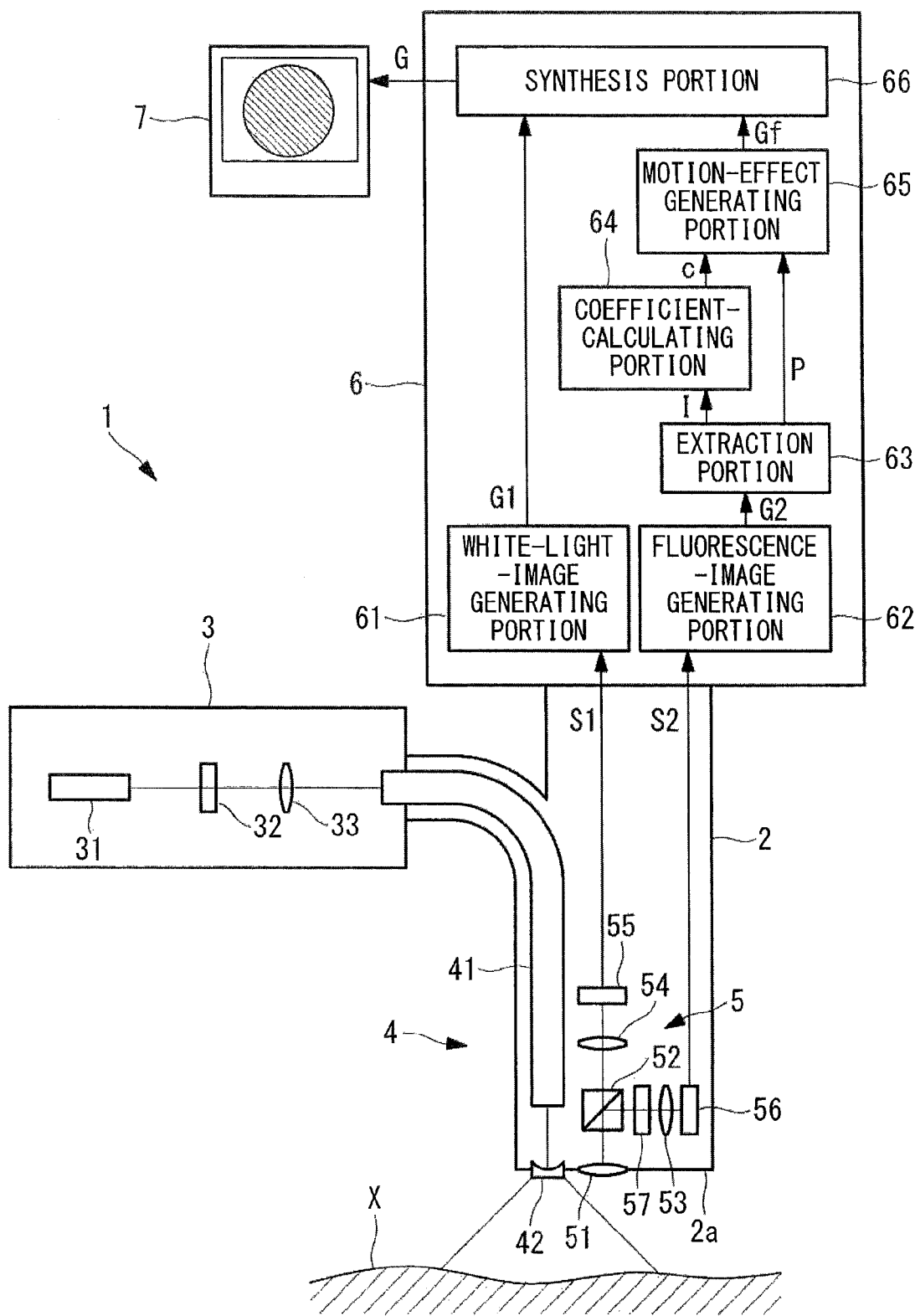
FIG. 1 is a diagram showing the overall configuration of a fluorescence observation apparatus according to one embodiment of the present invention.

The fluorescence observation apparatus 1 according to this embodiment is an endoscopic apparatus. As shown in FIG. 1, the fluorescence observation apparatus 1 includes an elongated insertion portion 2 that is inserted into a body; a light source 3; an illumination unit 4 that radiates excitation light and white light (reference light) from the light source 3 from a distal end 2a of the insertion portion 2 toward a subject X; an image-acquisition unit 5 that is provided in the distal end 2a of the insertion portion 2 and that acquires image information S1 and S2 of the subject X; an image processor 6 that is disposed at the base end of the insertion portion 2 and that processes the image information S1 and S2 acquired by the image-acquisition unit 5; and a display portion 7 that displays an image G which has been processed by the image processor 6.

The light source 3 includes a xenon lamp 31; a filter 32 that extracts excitation light and white light from the light emitted from the xenon lamp 31; and a coupling lens 33 that focuses the excitation light and the white light extracted by the filter 32. The filter 32 selectively transmits light with a wavelength band of 400 nm to 740 nm corresponding to the excitation light and white light. In other words, near-infrared light (e.g. a wavelength band of 700 nm to 740 nm) is used as the excitation light in this embodiment.

The illumination unit 4 includes a light guide fiber 41 that is disposed along almost the entire length in the longitudinal direction of the insertion portion 2 and an illumination optical system 42 that is provided at the distal end 2a of the insertion portion 2. The light guide fiber 41 guides the excitation light and the white light focused by the coupling lens 33. The illumination optical system 42 spreads out the excitation light and the white light that have been guided by the light guide fiber 41, and radiates them onto the subject X that faces the distal end 2a of the insertion portion 2.

The image-acquisition unit 5 includes an objective lens 51 that collects light from the subject X; a dichroic mirror 52 that reflects excitation light and fluorescence among the light collected by the objective lens 51 and that transmits white light (with a wavelength band of 400 nm to 700 nm; return light) having a wavelength shorter than that of the excitation light; two focusing lenses 53 and 54 that respectively focus the fluorescence reflected by the dichroic mirror 52 and the white light transmitted through the dichroic mirror 52; an image-acquisition device 55, such as a color CCD, that captures the white light focused by the focusing lens 54; and an image-acquisition device 56, such as a highly sensitive monochrome CCD, that captures the fluorescence focused by the focusing lens 53. In the figure, reference sign 57 refers to an excitation-light cutting filter that selectively transmits fluorescence (e.g., a wavelength band of 760 nm to 850 nm) among the light reflected by the dichroic mirror 52 and that blocks excitation light.

Based on the combination of the filter 32, the dichroic mirror 52, and the excitation-light cutting filter 67 having such wavelength characteristics, a white-light image G1 and a fluorescence image G2 can simultaneously be acquired, for example, by administering an anti-CEA antibody labeled with a fluorescent dye Cy7 to the subject X, followed by observation. CEA is a protein that is expressed specifically in cancer.

Figure 2:
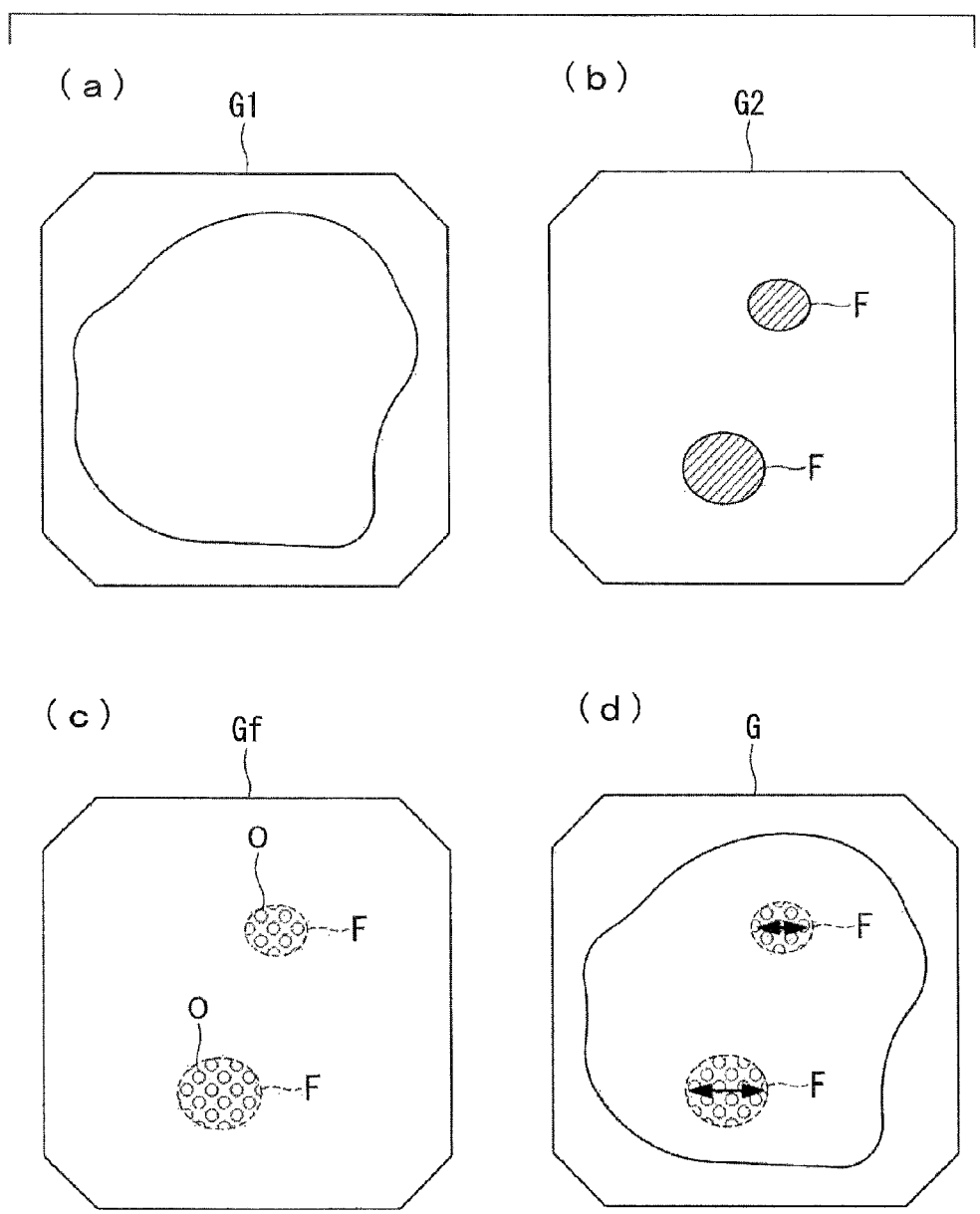
FIG. 2 shows (a) a white-light image, (b) a fluorescence image, (c) a frame image, and (d) a synthetic image that are generated in an image-processing unit of the fluorescence observation apparatus in FIG. 1.

The image processor 6 includes a white-light-image generating portion (reference-image generating portion) 61 that generates a white-light image (reference image) G1 from white-light image information S1 acquired by the image-acquisition device 55; a fluorescence-image generating portion 62 that generates a fluorescence image G2 from fluorescence image information S2 acquired by the image-acquisition device 56; an extraction portion 63 that extracts a fluorescence region F from the fluorescence image G2 generated by the fluorescence-image generating portion 62; a coefficient-calculating portion 64 that calculates a coefficient c for generation of a frame image Gf described below by use of a gradation value of the fluorescence region F extracted by the extraction portion 63; a motion-effect generating portion 65 that generates a frame image Gf time-varying at the position of the fluorescence region F; and a synthesis portion 66 that adds the frame image Gf generated by the motion-effect generating portion 65 to the white-light image G1 to generate a synthetic image G. FIG. 2 (a)-(d) show different types of images G1, G2, Gf, and G that are generated in image-processing in the image processor 6.

The image processor 6 includes a central processing unit (CPU), a main storage device such as RAM (Random Access Memory), and an auxiliary storage device. The auxiliary storage device is a non-transitory computer-readable storage medium such as an optical disc or a magnetic disk, and stores an image processing program. The CPU loads the image processing program stored in the auxiliary storage device, and then executes the program, thereby to implement functions of the white-light-image generating portion 61, the fluorescence-image generating portion 62, the extraction portion 63, the coefficient-calculating portion 64, the motion-effect generating portion 65, and the synthesis portion 66. Alternatively, the functions of those portions 61, 62, 63, 64, 65 and 66 may be implemented by hardware such as ASIC (Application Specific Integrated Circuit).

The extraction portion 63 compares the gradation value of each pixel of the fluorescence image G2 input from the fluorescence-image generating portion 62 with a prescribed threshold S, and extracts pixels having a gradation value equal to or higher than the prescribed threshold S as a fluorescence region F, as shown in (b) of FIG. 2. The extraction portion 63 outputs gradation values of the extracted pixels to the coefficient-calculating portion 64 and outputs positions of the extracted pixels to the motion-effect generating portion 65.

The coefficient-calculating portion 64 calculates a mean m of gradation values of pixels, constituting the fluorescence region F, that have been input by the extraction portion 63, calculates a coefficient c based on the calculated mean m, and outputs the calculated coefficient c to the motion-effect generating portion 65. The coefficient c is set as a function that increases with an increase of the mean m, for example, a function proportional to the mean m.

The coefficient-calculating portion 64 may calculate the coefficient c by use of a median or mode of gradation values of pixels extracted by the extraction portion 63, instead of using the mean m.

The motion-effect generating portion 65 has a clock that counts time t. The motion-effect generating portion 65 generates the frame image Gf constituting an animation that moves with a motion quantity (variation quantity) based on the coefficient c as time t passes, depending on the time t counted by the clock.

Specifically, the motion-effect generating portion 65 generates the frame image Gf displaying a predetermined object O within a region corresponding to the fluorescence region F, as shown in (c) of FIG. 2, based on positions of pixels input by the extraction portion 63. In other words, the frame image Gf has a gradation value in pixels that constitute the object O. The gradation value may be any prescribed value, or may be a value set based on the gradation value of the fluorescence region F.

In (c) of FIG. 2, as one example of the predetermined object O, a plurality of circles that have a certain dimension and that are arranged at a regular interval are shown. The motion-effect generating portion 65 creates a frame image Gf generating an animation in which the circles move within the fluorescence region F over time t when the frame image Gf is continuously displayed.

The motion quantity means the amplitude and speed of motion of the object O, and is set as a function that increases with an increase of the coefficient c, for example, a function proportional to the coefficient c. As the coefficient c becomes larger, i.e. as the gradation value of the fluorescence region F becomes larger, the motion-effect generating portion 65 generates a frame image Gf to make at least one of the amplitude and the speed of the motion of the object O larger.

The synthesis portion 66 adds the frame image Gf input from the motion-effect generating portion 65 to any of a red (R)-component image, a green (G)-component image, and a blue (B)-component image, for example, to the G-component image, that constitute the white-light image G1 input from the white-light-image generating portion 61. Specifically, the synthesis portion 66 adds gradation values of respective pixels of the frame image Gf to gradation values of respective pixels of the G-component image. Then, the synthetic image G is synthesized from the G-component image to which the frame image Gf has been added, as well as the other two, that is, the R-component image and the B-component image, and the generated synthetic image G is output to the display portion 7.

Next, the operation of the fluorescence observation apparatus 1 configured in such a manner will be described. In order to observe biological tissue inside the body, which is the subject X, by using the fluorescence observation apparatus 1 according to this embodiment, a fluorescence substance that accumulates in the lesion is preliminarily administered to the subject X. Then, the insertion portion 2 is inserted into the body so that its distal end 2a is disposed facing the subject X, and excitation light and white light are radiated from the distal end 2a of the insertion portion 2 to the subject X by operation of the light source 3.

In the subject X, the fluorescent substance included in the lesion is excited by the excitation light, thereby emitting fluorescence therefrom, and white light is reflected at the surface of the subject X. Portions of the fluorescence emitted from the subject X and the reflected white light return to the distal end 2a of the insertion portion 2, and are collected by the objective lens 51.

White light among the light collected by the objective lens 51 passes through the dichroic mirror 52, is focused by the focusing lens 54, and is acquired as white-light image information S1 by the image-acquisition device 55. Meanwhile, the fluorescence collected by the objective lens 51 is reflected by the dichroic mirror 52, and excitation light is removed therefrom by the excitation-light cutting filter 57. Then, the fluorescence is focused by the focusing lens 53 and is acquired as fluorescence image information S2 by the image-acquisition device 56. Image information S1 and S2 acquired by the respective image-acquisition devices 55 and 56 are delivered to the image processor (processor) 6.

Figure 3:
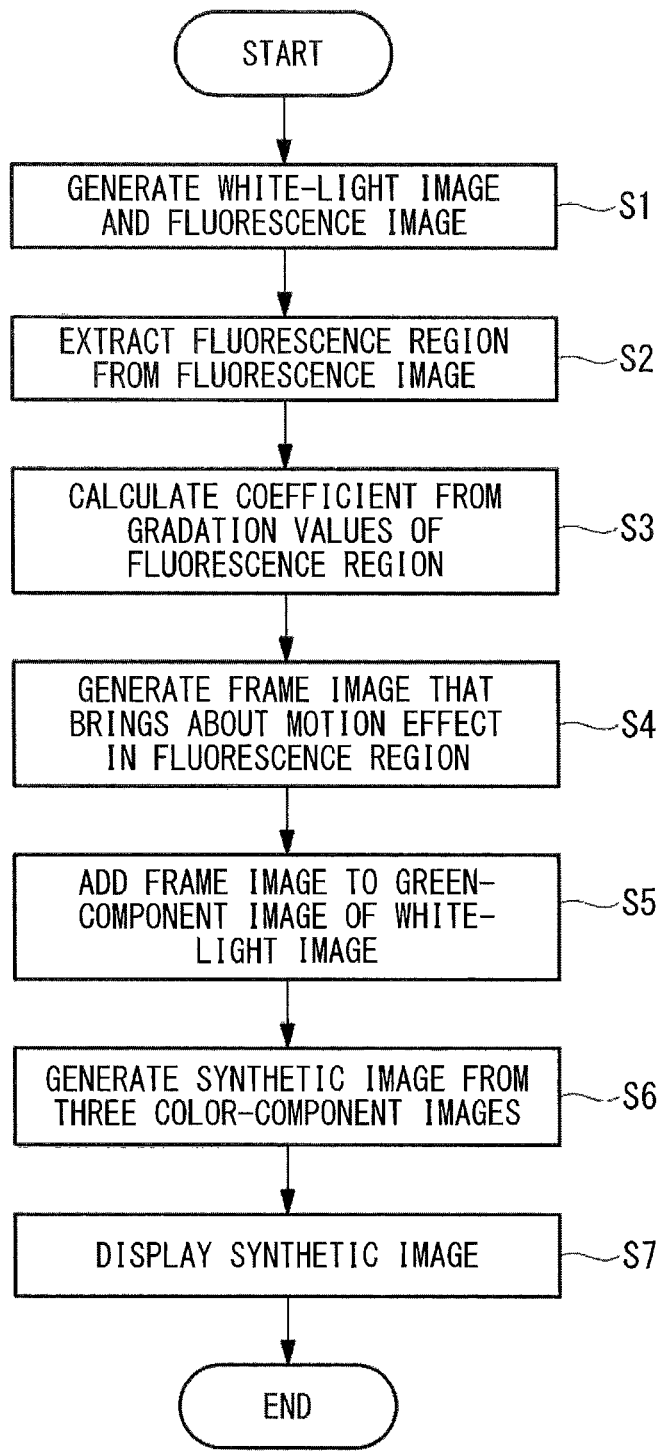
FIG. 3 is a flowchart illustrating processing in the image-processing unit in FIG. 1.
Figure 4:
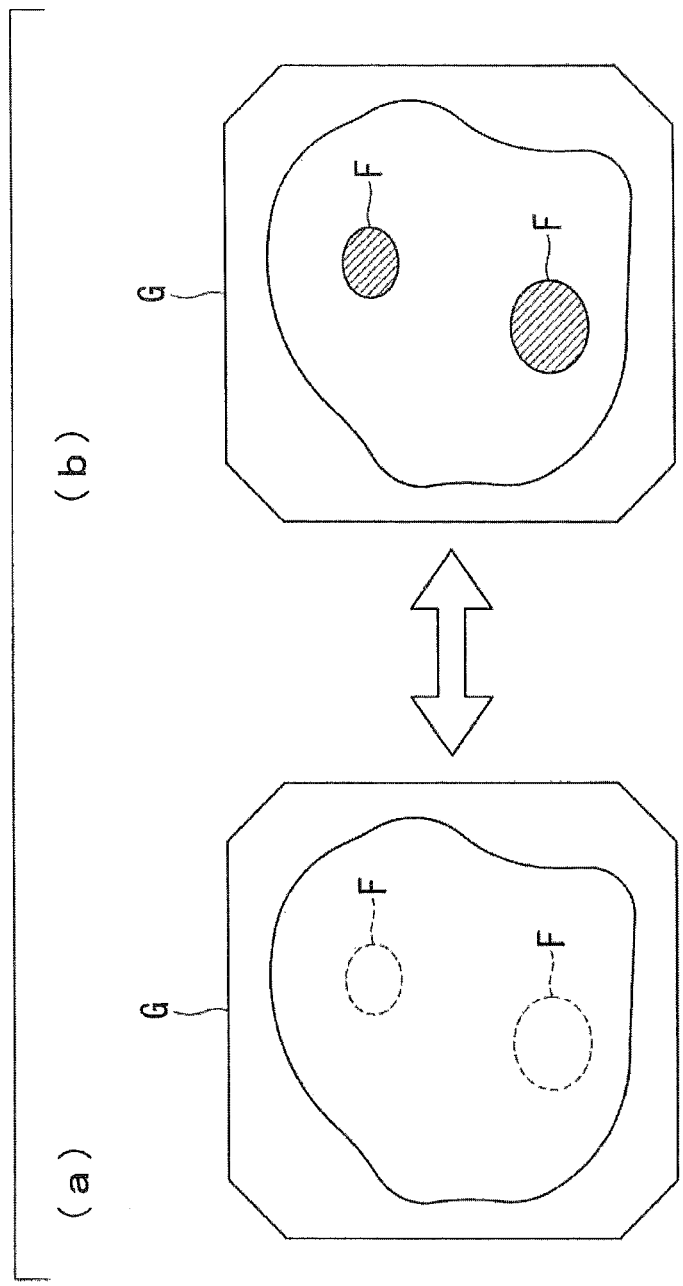
FIG. 4 is a modification of a synthetic image generated in the image-processing unit of the fluorescence observation apparatus in FIG. 1, and shows (a) a case where the gradation value is minimum and (b) a case where the gradation value is maximum.
Figure 5:
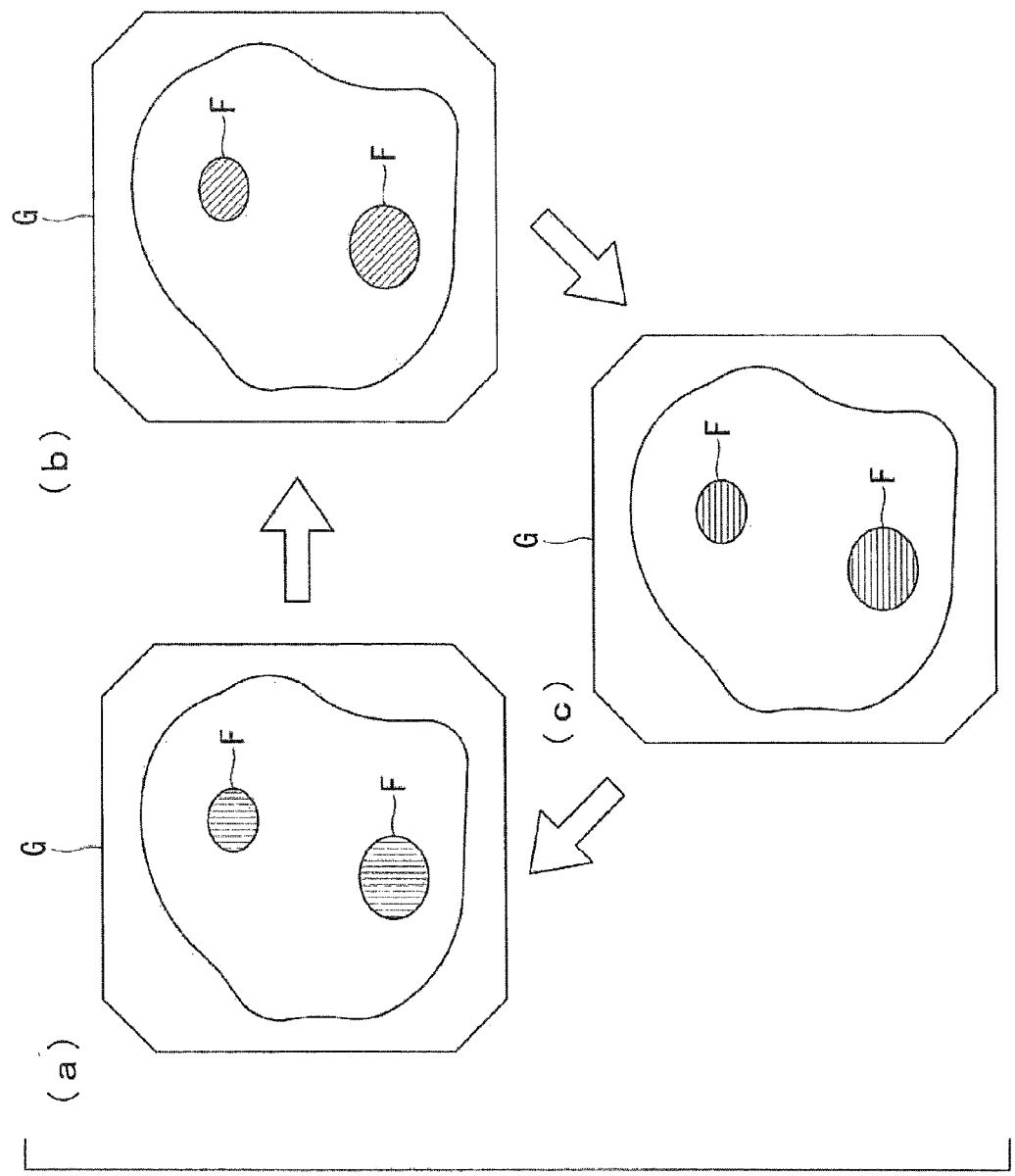
FIG. 5 is a modification of a synthetic image generated in the image-processing unit of the fluorescence observation apparatus in FIG. 1, and shows (a) a case where the hue is red, (b) a case where the hue is green, and (c) a case where the hue is blue.

A flowchart illustrating image-processing in the image processor 6 is shown in FIG. 3.

In the image processor 6, the white-light image information S1 is input to the white-light-image generating portion 61, thus generating the white-light image G1, and the fluorescence image information S2 is input to the fluorescence-image generating portion 62, thus generating the fluorescence image G2 (Step S1).

The fluorescence image G2 is delivered to the extraction portion 63, and a fluorescence region F having gradation values equal to or higher than a prescribed threshold S is extracted (Step S2). Gradation values of respective positions of the extracted fluorescence region F are delivered to the coefficient-calculating portion 64 and position information of the fluorescence region F are delivered to the motion-effect generating portion 65. Then, in the coefficient-calculating portion 64, a mean m of gradation values of the fluorescence region F is calculated from gradation values delivered from the extraction portion 63, and a coefficient c is further calculated from the mean m (Step S3).

Then, in the motion-effect generating portion 65, a frame image Gf displaying a predetermined object O at the position of the fluorescence region F is generated based on the time t and the coefficient c (Step S4). Then, in the synthesis portion 66, the frame image Gf is added to a G-component image of the three component images that constitute the white-light image G1 (Step S5), a color synthetic image G is generated by use of the G-component image to which the frame image Gf has been added, as well as a raw R-component image and a raw B-component image (Step S6), and the generated synthetic image G is displayed on the display portion 7 (Step S7).

In the synthetic image G continuously displayed on the display portion 7, the predetermined object O included in the synthetic image G produces a motion effect. In other words, an animation in which a predetermined green object O moves with a motion quantity depending on the gradation value of the fluorescence region F is displayed in a region corresponding to the fluorescence region F in the synthetic image G.

Thus, according to this embodiment, the animation in which the predetermined object O moves is displayed at the position of the lesion within the synthetic image G on the display portion 7 that the observer is observing. The observer can easily recognize the lesion by the predetermined object O that is moving. Furthermore, the observer can intuitively and easily recognize fluorescence intensities, i.e., pathological severity in the lesion, based on the amplitude or speed of the motion of the predetermined object O. Additionally, gradation values of three color-component images that constitute the white-light image G1, i.e. information on the morphology of the subject X, are included in the region of the synthetic image G where the object O is displayed. Therefore, even when the object O is displayed at the position of the lesion in the synthetic image G, the morphology of the lesion can be observed with sufficient clearness.

In this embodiment, it is assumed that the frame image Gf is added to the G-component image of the white-light image G1. However, instead of this, the frame image Gf may be added to the R-component image or the B-component image. Alternatively, the frame image Gf may be divided and added to a plurality of component images. For example, gradation values of the frame image may be divided and added to the G-component image and the B-component image at a ratio of 2:1.

In this embodiment, the motion-effect generating portion 65 is assumed to impart a spatial motion effect to a region of the lesion within the synthetic image G. However, the aspect for the motion effect that the motion-effect generating portion 65 imparts to the region of the lesion is not limited thereto, and, as long as the motion effect is an effect causing a visual variation over time, such an effect is sufficient. For example, the motion-effect generating portion 65 may generate a frame image that is assigned a gradation value that causes the color to vary over time within the region of the lesion, thus providing an effect causing the color to vary with a time period or with a range depending on the gradation values of the fluorescence region F. Additionally, such an color variation effect may be combined with the above-described motion effect of the object O. In this case, the color variation refers to variation of hues, intensity, brightness or contrast of color.

Thus, as an alternative to or besides spatial motion, such a color variation effect may also be provided to allow the observer to easily recognize the lesion. Additionally, the time period or range of the color variation can be set depending on the gradation values of the fluorescence region F to thereby allow the observer to intuitively and easily recognize the pathological severity of the lesion.

In this case, the relation among the synthetic image G, the white-light image G1, and the frame image Gf in the region to which the color variation effect is imparted is defined by a matrix generally represented as formula (1). In formula (1), R', G', and B' are gradation values of the R-component, the G-component, and the B-component, respectively, of the synthetic image G. R, G, and B are gradation values of the R-component, the G-component, and the B-component, respectively, of the white-light image G1. Each component represented by sin is a gradation value of each color component of the frame image Gf. A, B and C are 0 or the coefficient c.

{Math. 1}

$$\begin{pmatrix} R' \\ G' \\ B' \end{pmatrix} = \begin{pmatrix} 1 & 0 & 0 & A\sin(\alpha t + \phi_R) \\ 0 & 1 & 0 & B\sin(\beta t + \phi_G) \\ 0 & 0 & 1 & C\sin(\gamma t + \phi_B) \end{pmatrix} \begin{pmatrix} R \\ G \\ B \\ 1 \end{pmatrix} \quad (1)$$

Speaking of cases where a color-contrast variation effect is provided, when letting $\phi_R=\phi_G=\phi_B=0$, all gradation values of the R-component, the G-component, and the B-component vary in the same phase in the frame image Gf. Further, when letting A=C=0, B=c and β=1, a gradation value of the G-component of the frame image Gf that periodically varies with a range proportional to the coefficient c is added to a gradation value of the G-component image. Accordingly, as shown in (a) and (b) of FIG. 4, the fluorescence region F blinks between a transparent color and a dark green in the synthetic image G. On the other hand, when letting A=C=0, B=1 and β=c, the gradation value of the G-component of the frame image Gf that periodically varies with a speed proportional to the coefficient c is added to the G-component image. Accordingly, the fluorescence region F blinks in the synthetic image G. In contrast, when letting A=−1, B=1, C=0 and α=β=1, the gradation value of the R-component and the gradation value of the G component of the frame image Gf that vary in phases opposite to one another are added to the R-component image and the G-component image, respectively, of the white-light image G1. In this case, when the gradation value of the G-component is maximum in the synthetic image G, the gradation value of the R-component is minimum, and the hue of the fluorescence region F varies alternately between red and green.

Speaking of cases where a hue variation effect is provided, when values that are different from each other are assigned to $\phi_R$, $\phi_G$ and $\phi_B$, gradation values of the R component, the G component, and the B component vary with different phases from one another in the frame image Gf. For example, when letting $\phi_R=0$, $\phi_G=2\pi/3$, and $\phi_B=4\pi/3$, as well as A=B=C=1 and α=β=γ=c, as shown in (a) to (c) of FIG. 5, the hue of the fluorescence region F in the synthetic image G varies in the order red, green and blue with a time period proportional to the coefficient c. On the other hand, when letting A=B=C=c and α=β=γ=1, the hue of the fluorescence region F in the synthetic image G varies with a range proportional to the coefficient c. In (a) to (c) of FIG. 5, differences in the hatching directions represent differences in the hue.

Next, modifications of the above-described fluorescence observation apparatus 1 according to this embodiment will be described.

(First Modification)

Figure 6:
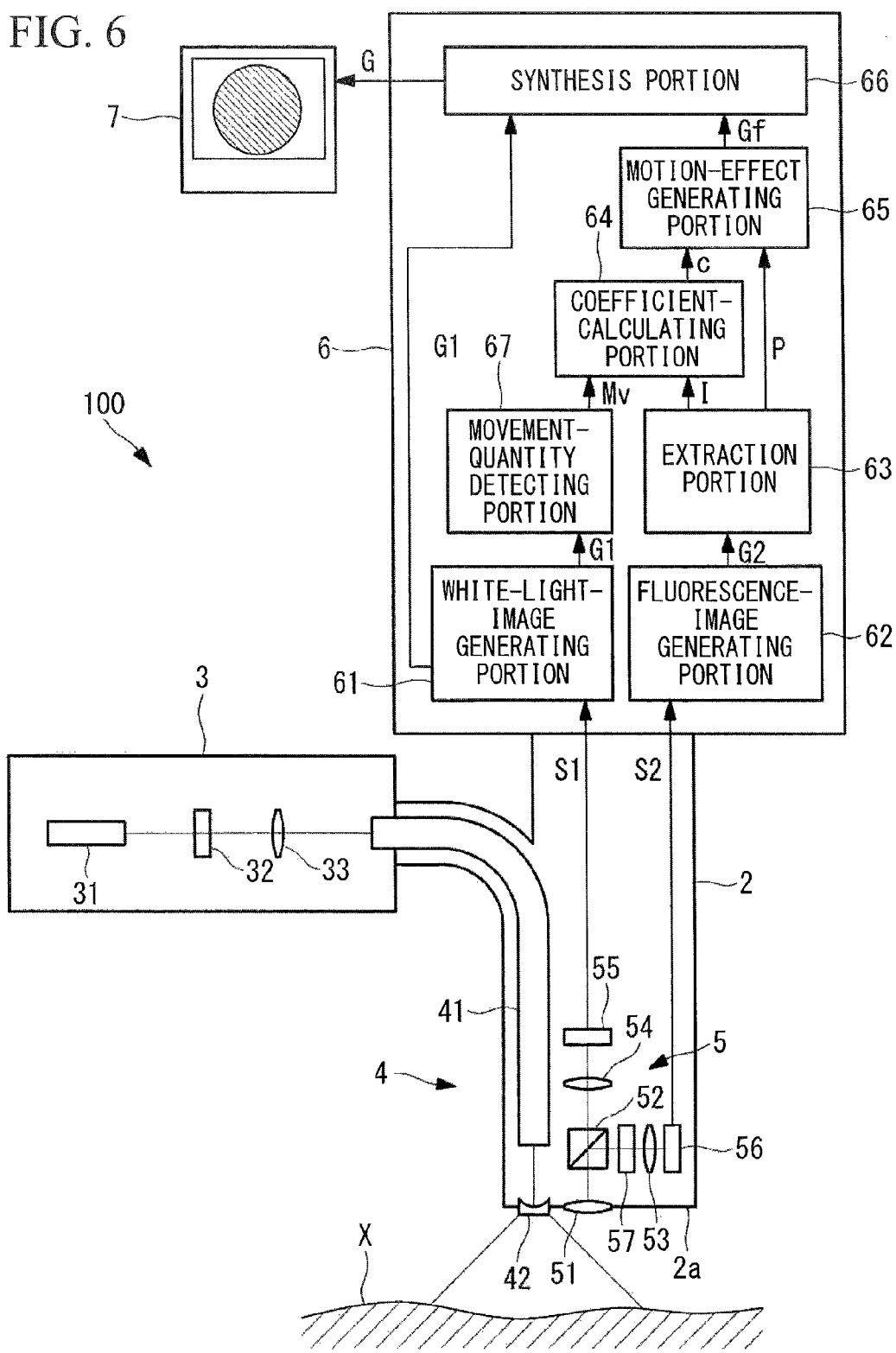
FIG. 6 is an overall configuration diagram of a first modification of the fluorescence observation apparatus in FIG. 1.

As shown in FIG. 6, a fluorescence observation apparatus 100 according to a first modification of this embodiment further includes a movement-quantity detecting portion 67 that detects a movement quantity of a subject X within a white-light image G1.

The movement-quantity detecting portion 67 calculates a movement quantity Mv between a distal end 2a of an insertion portion 2 and the subject X by using well-known techniques such as, for example, by extracting a characteristic region from the white-light image G1 and calculating of a motion vector of the extracted characteristic region. Then, the movement-quantity detecting portion 67 outputs the calculated movement quantity Mv to a coefficient-calculating portion 64.

The coefficient-calculating portion 64 calculates a coefficient c' based on the movement quantity Mv input from the movement-quantity detecting portion 67 and a mean m of gradation values of a fluorescence region F input from an extraction portion 63. For example, the coefficient-calculating portion 64 adds the movement quantity Mv to the above-described coefficient c to thereby calculate a coefficient c'.

Figure 7:
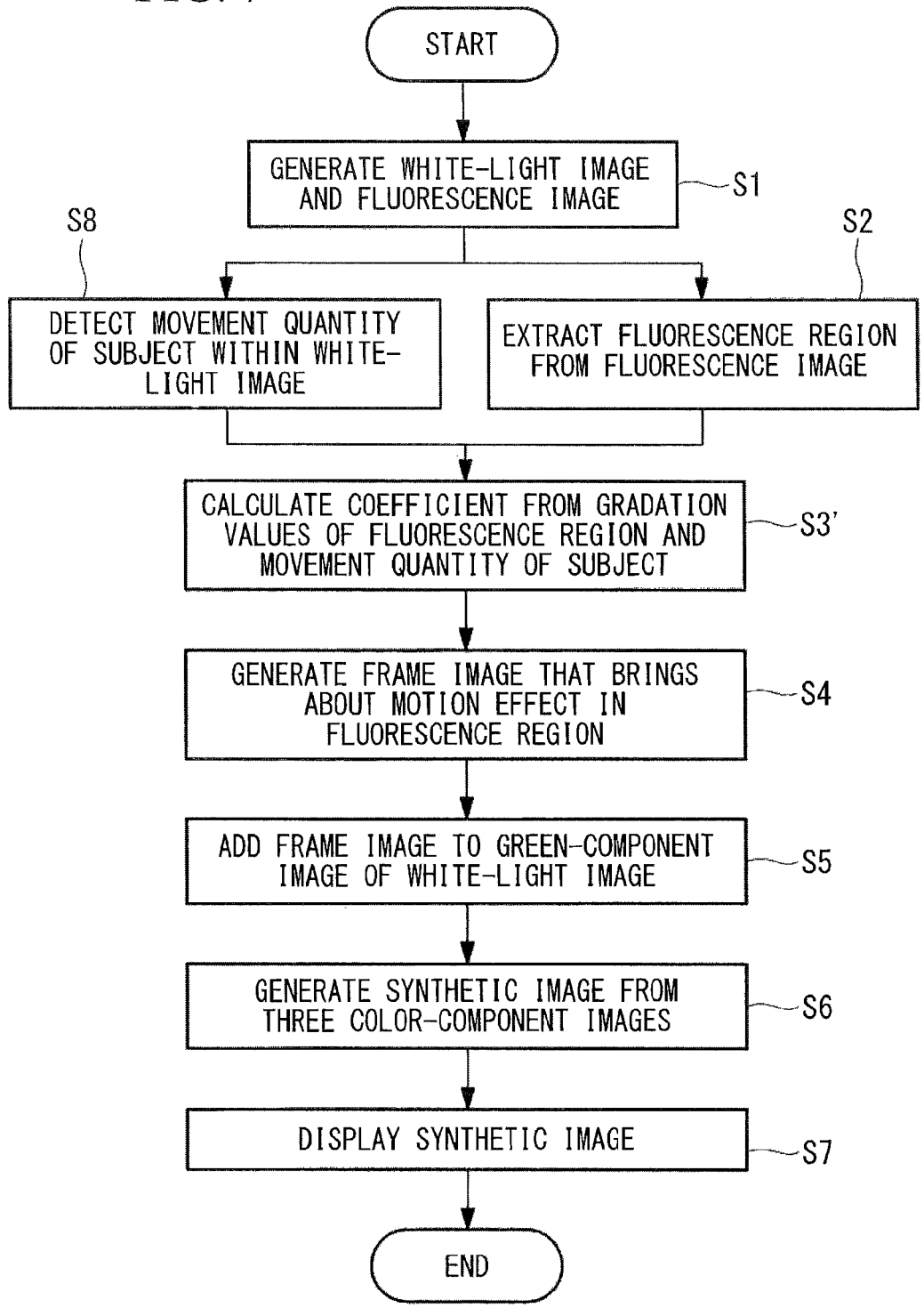
FIG. 7 is a flowchart illustrating processing in the image-processing unit in FIG. 6.

The operation of the fluorescence observation apparatus 100 configured in such a manner will be described with reference to FIG. 7.

In the this modification, the movement quantity Mv of the subject X within the white-light image G1 generated in Step S1 is detected from the white-light image G1 (Step S8). In next Step S3', the coefficient c' is calculated by also taking into consideration the detected movement quantity Mv. In Step S4, the frame image Gf is generated by using the coefficient c' instead of using the coefficient c. Subsequent processing is identical to FIG. 3, and therefore, descriptions thereof are omitted.

Thus, according to this modification, when the subject X is moved within the white-light image G1 based on relative movement of the distal end 2a of the insertion portion 2 and the subject X, the motion quantity of the object O varies depending on the movement quantity Mv. In other words, relative to a motion quantity in a case where the viewing field of the white-light image G1 is constant, the motion quantity in a case where a viewing field of the white-light image G1 is moving is larger. In such a way, by varying the motion quantity of the object O relative to the motion quantity of the subject X, motion of the object O is sufficiently accentuated against the moving subject X, thereby allowing the observer to reliably recognize the lesion.

(Second Modification)

Figure 8:
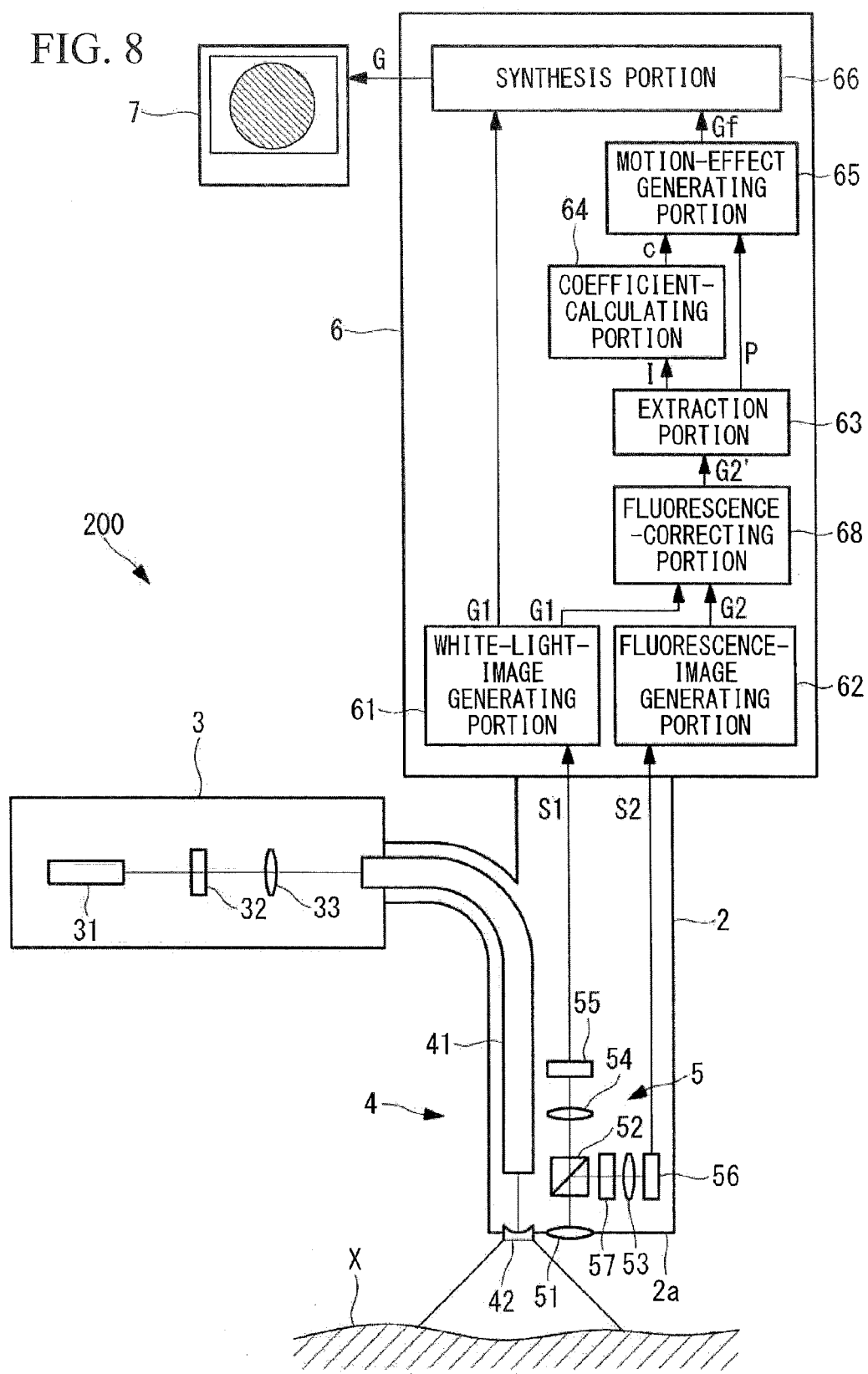
FIG. 8 is an overall configuration diagram of a second modification of the fluorescence observation apparatus in FIG. 1.

As shown in FIG. 8, a fluorescence observation apparatus 200 according to the second modification of this embodiment further includes a fluorescence-correcting portion 68 that corrects a fluorescence image G2 generated by a fluorescence-image generating portion 62 by use of a white-light image G1 generated by a white-light image-generating part 61. The fluorescence-correcting portion 68 divides gradation values of respective pixels of the fluorescence image G2 input from the fluorescence-image generating portion 62 by gradation values of respective pixels of the white-light image G1 input from the white-light-image generating portion 61 to thereby generate a corrected fluorescence image G2' in which gradation values are corrected, and outputs the generated corrected fluorescence image G2' to an extraction portion 63.

The extraction portion 63 extracts a fluorescence region F from the corrected fluorescence image G2' instead of the fluorescence image G2.

Figure 9:
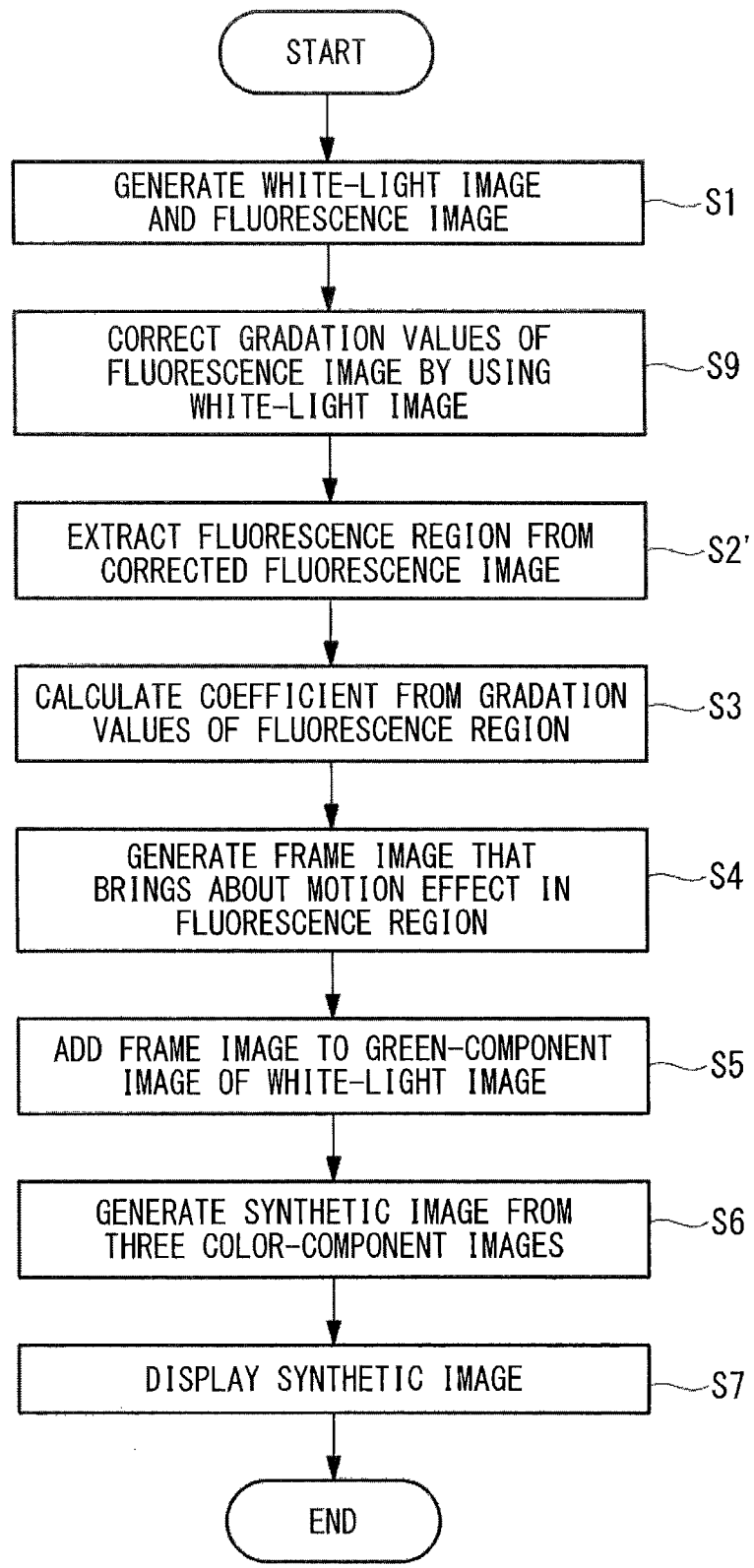
FIG. 9 is a flowchart illustrating processing in the image-processing unit in FIG. 8.

The operation of the fluorescence observation apparatus 200 configured in such a manner will be described with reference to FIG. 9.

In the present modification, a gradation value of the fluorescence image G2 generated in Step S1 is corrected with a gradation value of the white-light image G1 (Step S9). In the subsequent Step S2', a fluorescence region F is extracted from the corrected fluorescence image G2' in which the gradation values have been corrected. Subsequent processing is identical to FIG. 3, and therefore, descriptions thereof are omitted.

Thus, according to the present modification, the corrected fluorescence image G2' in which gradation values have been normalized by using the white-light image G1 is an image in which changes of gradation values depending on an observation distance and an observation angle between the distal end 2a of the insertion portion 2 and the subject X have been eliminated and in which original intensities of fluorescence emitted from each position of the subject X are more accurately reflected. The extraction portion 63 can extract the lesion as a fluorescence region F even more accurately by using such a corrected fluorescence image G2' instead of an unprocessed fluorescence image G2. Additionally, the motion-effect generating portion 65 can provide the fluorescence region F with a motion quantity that still more-accurately represents the pathological severity of the lesion.

(Third Modification)

Figure 10:
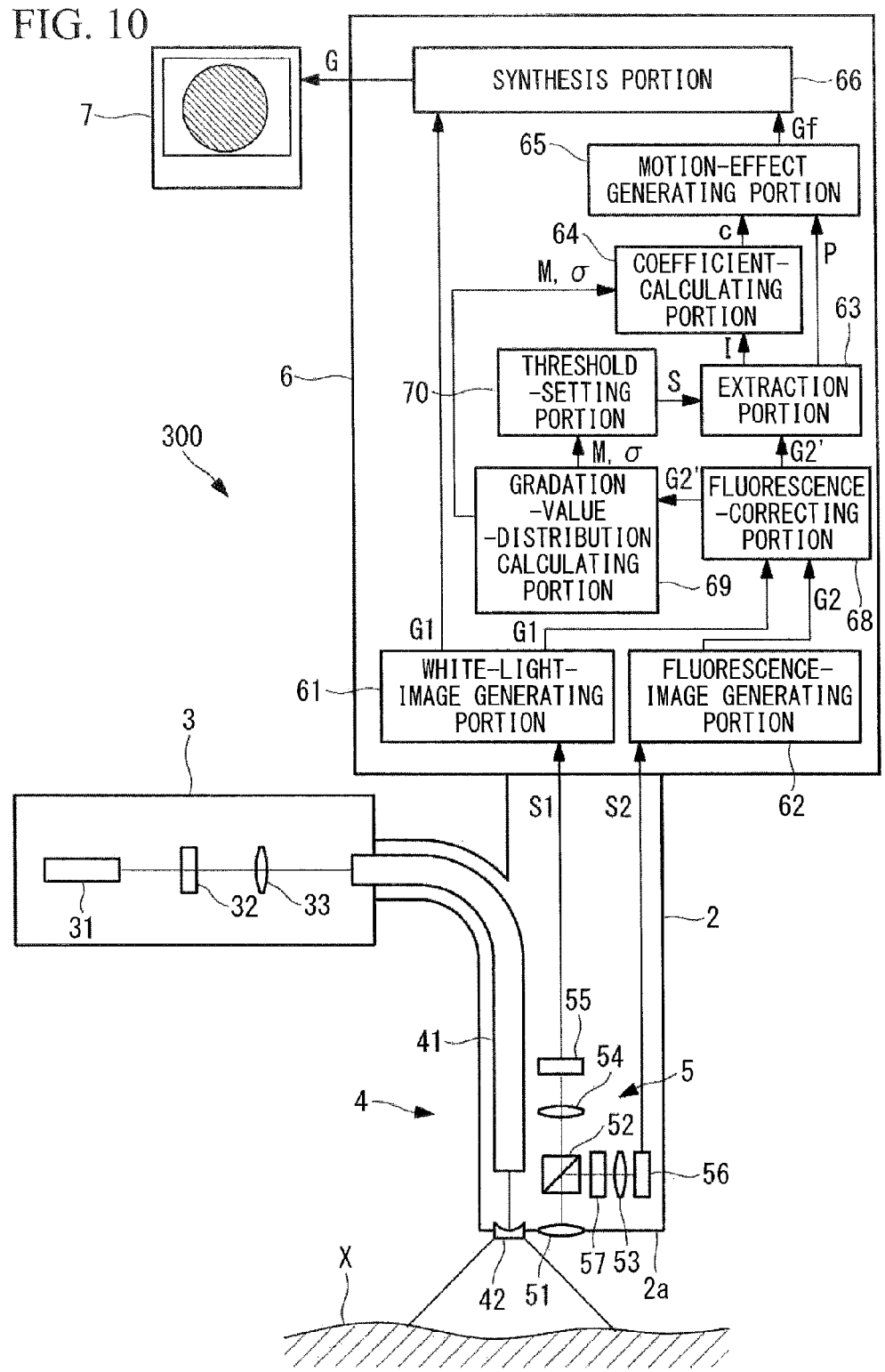
FIG. 10 is an overall configuration diagram of a third modification of the fluorescence observation apparatus in FIG. 1.

A fluorescence observation apparatus 300 according to a third modification of this embodiment is one that is obtained by further modifying the second modification, and further includes a gradation-value-distribution calculating portion 69 that calculates the distribution of gradation values in the corrected fluorescence image G2' and a threshold-setting portion 70 that sets a threshold S in an extraction portion 63, as shown in FIG. 10.

The gradation-value-distribution calculating portion 69 calculate a mean M and a standard deviation σ of gradation values of the corrected fluorescence image G2' based on the distribution of gradation values of the entirety of or a predetermined portion of the region of the corrected fluorescence image G2', and outputs the resulting mean M and standard deviation σ to the threshold-setting portion 70 and a coefficient-calculating portion 64.

For example, as shown in the following formula (2), the threshold-setting portion 70 calculates a threshold S from a sum of the mean M and the standard deviation σ of gradation values. Then, the threshold-setting portion 70 sets the calculated threshold S as a prescribed threshold S for extracting the fluorescence region F in the extraction portion 63. Here, a and b are coefficients that are set so as to decrease with an increase in the proportion of a region of a predetermined gradation value or higher occupying the corrected fluorescence image G2'.

$$S = aM + b\sigma \quad (2)$$

The coefficient-calculating portion 64 uses m, M and σ to calculate a coefficient c, for example, from the following formula (3).

$$C = (m-M)/\sigma \quad (3)$$

Figure 11:
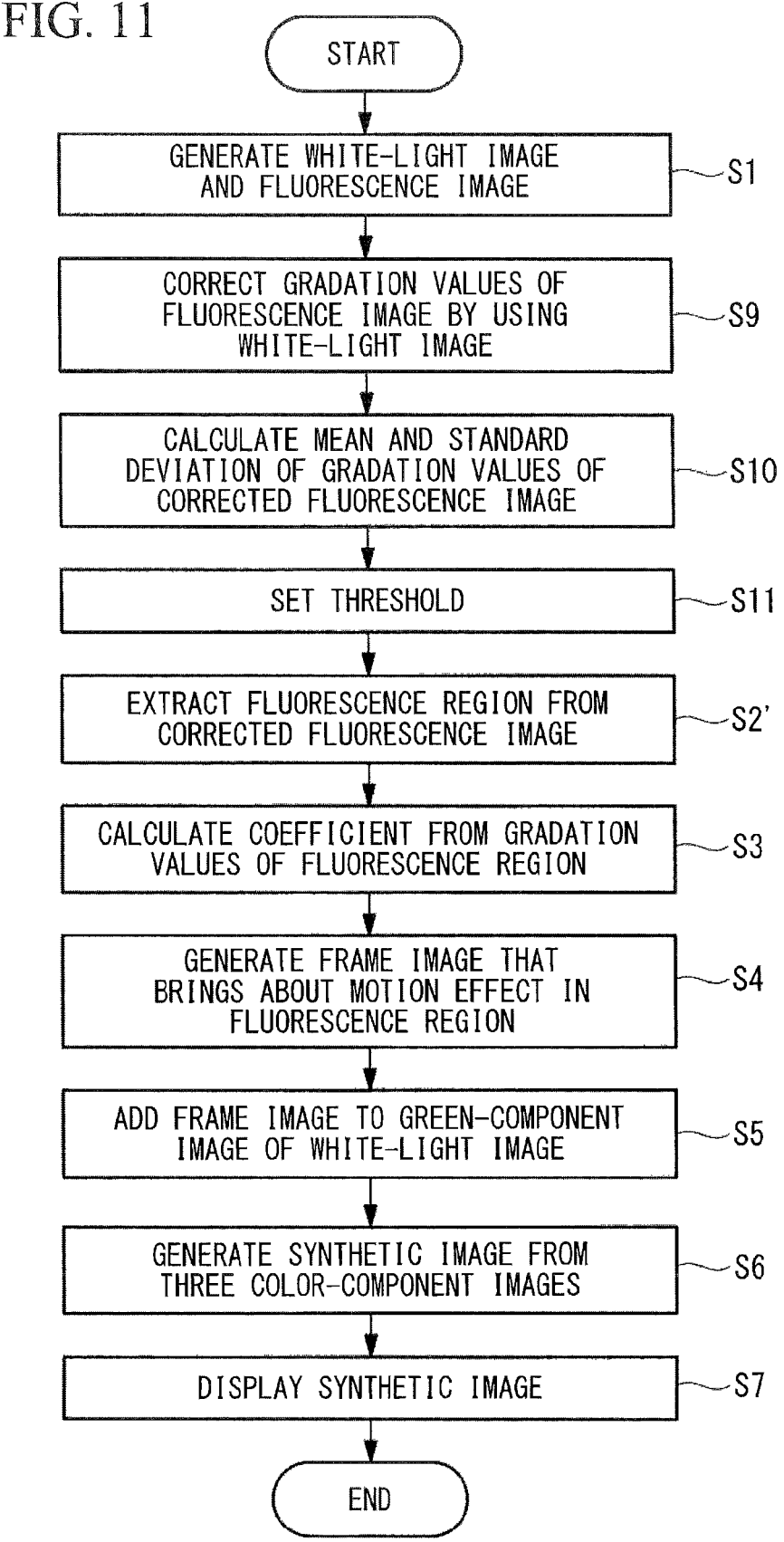
FIG. 11 is a flowchart illustrating processing in the image-processing unit in FIG. 10.

The operation of the fluorescence observation apparatus 300 configured in such a manner will be described with reference to FIG. 11.

In the present modification, after the corrected fluorescence image G2' is generated in Step S9, a mean M and a standard deviation σ of gradation values of the corrected fluorescence image G2' are calculated (Step S10), and a threshold S that is used in the extraction portion 63 is set based on the values of M and σ (Step S11). In subsequent Step S2', a fluorescence region F having a gradation value equal to or higher than the threshold S set in Step S11 is extracted from the corrected fluorescence image G2'. Subsequent processing is identical to FIG. 3, and therefore, descriptions thereof are omitted.

Thus, according to the present modification, the threshold S, which is used in the extraction portion 63, and the coefficient c, which is used in the motion-effect generating portion 65, vary depending on the distribution of gradation values of the corrected fluorescence image G2'. Accordingly, even when there is a remaining variation of gradation values that depends on the observation distance and the observation angle, in the corrected fluorescence image G2', the lesion can always accurately be extracted. Additionally, even when there is variability among gradation values of respective pixels in the corrected fluorescence image G2', an even more highly accurate threshold S can be set. As a result, accuracy of extraction of the lesion can further be improved.

REFERENCE SIGNS LIST 1, 100, 200, 300 Fluorescence observation apparatus
2 Insertion portion
3 Light source
31 Xenon lamp
32 Filter
33 Coupling lens
4 Illumination unit
41 Light guide fiber
42 Illumination optical system
5 Image-acquisition unit
51 Objective lens
52 Dichroic mirror
53, 54 Focusing lens
55, 56 Image-acquisition device
57 Excitation-light cutting filter
6 image processor (processor)
61 White-light-image generating portion (reference-image generating portion)
62 Fluorescence-image generating portion
63 Extraction portion
64 Coefficient-calculating portion
65 Motion-effect generating portion
66 Synthesis portion
67 Movement-quantity detecting portion
68 Fluorescence-correcting portion
69 Gradation-value-distribution calculating portion
70 Threshold-setting portion
7 Display portion
G Synthetic image
G1 White-light image (reference image)
G2 Fluorescence image
G2' Corrected fluorescence image
Gf Frame image

The invention claimed is:

1. A fluorescence observation apparatus, comprising:
a light source configured to irradiate a subject with reference light and excitation light; and
one or more processors comprising hardware, wherein the one or more processors are configured to implement:
a fluorescence-image generating portion configured to generate a fluorescence image based on fluorescence produced in the subject due to irradiation with the excitation light;
a reference-image generating portion configured to generate a color reference image based on return light returning from the subject due to irradiation with the reference light;
an extraction portion configured to extract, from the fluorescence image generated by the fluorescence-image generating portion, a fluorescence region having a gradation value equal to or higher than a prescribed threshold;
a motion-effect generating portion configured to generate a frame image that is assigned a time-varying gradation value so as to bring about an effect that is visually time-varying with a variation quantity depending on a gradation value of the fluorescence region, in a region corresponding to the fluorescence region extracted by the extraction portion; and a synthesis portion configured to add the frame image generated by the motion-effect generating portion to at least one of a plurality of color-component images constituting the reference image, to synthesize a synthetic image from the plurality of color-component images comprising the color-component image that the frame image has been added to.

2. The fluorescence observation apparatus according to claim 1,
wherein the one or more processors are further configured to implement a coefficient-calculating portion configure to calculate a coefficient, which increases with an increase of the gradation value of the fluorescence region, based on said gradation value, and
wherein the motion-effect generating portion is configured to determine the variation quantity based on the coefficient calculated by the coefficient-calculating portion.

3. The fluorescence observation apparatus according to claim 1, wherein the motion-effect generating portion is configured to generate the frame image that brings about an effect causing a predetermined object to move within the corresponding region at a speed depending on the gradation value of the fluorescence region.

4. The fluorescence observation apparatus according to claim 1, wherein the motion-effect generating portion is configured to generate the frame image that brings about an effect causing a predetermined object to move within the corresponding region with an amplitude depending on the gradation value of the fluorescence region.

5. The fluorescence observation apparatus according to claim 1, wherein the motion-effect generating portion is configured to generate the frame image that brings about an effect causing a color to vary with a period depending on the gradation value of the fluorescence region.

6. The fluorescence observation apparatus according to claim 1, wherein the motion-effect generating portion is configured to generate the frame image that brings about an effect causing a color to vary with a range depending on the gradation value of the fluorescence region.

7. The fluorescence observation apparatus according to claim 3,
wherein the one or more processors are further configured to implement a movement-quantity detecting portion configured to detect a movement quantity of the subject in the reference image, and
wherein the motion-effect generating portion is configured to generate the frame image that varies with a variation quantity depending on a value obtained by adding the movement quantity of the subject detected by the movement-quantity detecting portion to the gradation value of the fluorescence region.

8. The fluorescence observation apparatus according to claim 4,
wherein the one or more processors are further configured to implement a movement-quantity detecting portion configured to detect a movement quantity of the subject in the reference image, and
wherein the motion-effect generating portion is configured to generate the frame image that varies with a variation quantity depending on a value obtained by adding the movement quantity of the subject detected by the movement-quantity detecting portion to the gradation value of the fluorescence region.

9. The fluorescence observation apparatus according to claim 1,
wherein the one or more processors are further configured to implement a fluorescence-correcting portion configured to divide the fluorescence image generated by the fluorescence-image generating portion by the reference image generated by the reference-image generating portion to thereby correct the gradation value of the fluorescence image, and
wherein the extraction portion is configured to extract the fluorescence region from the fluorescence image corrected by the fluorescence-correcting portion.

10. The fluorescence observation apparatus according to claim 9, wherein the one or more processors are further configured to implement a threshold-setting portion configured to set the prescribed threshold in the extraction portion based on a sum of a mean of gradation values of respective pixels in the fluorescence image corrected by the fluorescence-correcting portion and a standard deviation of the gradation values.

* * * * *